(12) United States Patent
Stankovic et al.

(10) Patent No.: US 9,369,005 B2
(45) Date of Patent: Jun. 14, 2016

(54) ENERGY EXTRACTION

(71) Applicants: Massachusetts Eye & Ear Infirmary, Boston, MA (US); Massachusetts Institute of Technology, Cambridge, MA (US)

(72) Inventors: Konstantina Stankovic, Boston, MA (US); Anantha Chandrakasan, Belmont, MA (US); Patrick Mercier, San Diego, CA (US); Saurav Bandyopadhyay, Dallas, TX (US); Andrew Lysaght, Boston, MA (US)

(73) Assignees: Massachusetts Eye & Ear Infirmary, Boston, MA (US); Massachusetts Institute of Technology, Cambridge, MA (US)

( * ) Notice: Subject to any disclaimer, the term of this patent is extended or adjusted under 35 U.S.C. 154(b) by 193 days.

(21) Appl. No.: 14/195,371

(22) Filed: Mar. 3, 2014

(65) Prior Publication Data

US 2014/0247020 A1  Sep. 4, 2014

Related U.S. Application Data

(60) Provisional application No. 61/771,658, filed on Mar. 1, 2013.

(51) Int. Cl.
*H02J 7/00* (2006.01)
*H02J 7/32* (2006.01)
*A61F 2/10* (2006.01)

(52) U.S. Cl.
CPC ... *H02J 7/32* (2013.01); *A61F 2/10* (2013.01); *Y02B 40/90* (2013.01)

(58) Field of Classification Search
CPC ...................................... H02J 7/345
USPC ........................................... 320/166
See application file for complete search history.

(56) References Cited

U.S. PATENT DOCUMENTS

| | | | | |
|---|---|---|---|---|
| 2008/0262562 A1* | 10/2008 | Roberts | ............... | H02K 7/1876 607/35 |
| 2010/0076517 A1* | 3/2010 | Imran | ............... | A61N 1/362 607/35 |
| 2014/0277277 A1* | 9/2014 | Gordon | ............... | A61N 1/378 607/59 |
| 2015/0080981 A1* | 3/2015 | John | ............... | A61N 1/3785 607/59 |
| 2015/0306403 A1* | 10/2015 | Langer | ............... | A61N 1/3787 607/17 |
| 2016/0038738 A1* | 2/2016 | Naylor | ............... | A61N 1/0541 607/57 |
| 2016/0079855 A1* | 3/2016 | Ramorini | ............... | H02J 7/35 323/304 |

* cited by examiner

*Primary Examiner* — Suresh Memula
(74) *Attorney, Agent, or Firm* — Talem IP Law, LLP

(57) ABSTRACT

This disclosure describes techniques and systems for extracting energy from the endocochlear potential (EP) in animal subjects (e.g., human subjects) and using the extracted energy to operate circuits (e.g., electronic device, sensors, and transmitters). The subject matter of this disclosure is embodied, for example, in a system for extracting energy from an endocochlear potential of an animal, wherein the system includes a pair of electrodes, and a circuit coupled to the pair of electrodes. The circuit includes a boost converter, an energy buffer component configured to receive voltage from the boost converter, a start-up rectifier configured to provide voltage to the energy buffer component, and a control component configured to provide control signals to the boost converter. The power extracted from the endocochlear potential is equal or larger than the quiescent power of the circuit.

16 Claims, 10 Drawing Sheets

ENERGY EXTRACTION

CROSS-REFERENCE TO RELATED APPLICATION

This application claims the benefit under 35 U.S.C. §119 of Provisional Patent Application No. 61/771,658, filed Mar. 1, 2013, which is hereby incorporated by reference in its entirety.

GOVERNMENT SUPPORT

This invention was made with government support under Contract No. HR0011-13-3-0002 awarded by Defense Advanced Research Projects Agency (DARPA). The government has certain rights in the invention.

BACKGROUND OF THE INVENTION

Several known energy extracting (also referred as "harvesting") devices generate electricity based on motion resulting from muscle actuation. Such energy extracting techniques are based on induction (e.g., geared motion into a generator) or piezoelectricity (e.g., pressure or vibrational motion of a piezoelectric material). For example, heel-strike or leg-mounted harvesters are used to extract energy from muscle actuation. Another form of energy extraction is based on temperature differences, e.g., between the temperature of atmosphere and a live animal.

Another approach to energy extraction relies on chemical reactions. Such systems extract energy from glucose that is naturally found in blood. One example is microbial biofuel cell technology, which use precious metals and whole-cells as catalysts. Another example is enzymatic biofuel cell technology, which uses enzymes as catalysts.

BRIEF SUMMARY

This disclosure describes techniques and systems for extracting energy from the endocochlear potential (EP) in animal subjects (e.g., human subjects) and using the extracted energy to operate circuits (e.g., electronic device, sensors, and transmitters). In particular, such circuits can be implantable devices for medical applications, which may need to operate reliably over long periods of time. Because the extracted energy can be used to operate the circuits in a self-autonomous and/or self-sustainable manner, the new systems can avoid the need for implantable batteries (which may need surgical re-implantation) or external wireless power sources for long-term operation.

In some embodiments, the techniques and systems disclosed herein enable monitoring of an auditory system of an animal through long-term, autonomous, in vivo sensing of ions (e.g., $K^+$, $Na^+$, $H^+$, $Ca^{2+}$, and $Mg^{2+}$) and molecules (e.g., proteins, peptides, neurotransmitters, metabolites) in the cochlea. For example, energy from the EP can be extracted to power circuits without substantially affecting hearing performances. In addition, the systems and methods disclosed herein relate to implantable circuits that can be anatomically-sized and operate with ultra-low quiescent-power (e.g., 660 pW or less). Quiescent-power refers to the power consumed during standby (or inactive) mode of circuits or included components. In addition, energy extraction can occur in an in vivo manner, which enables long-term operation during normal activity of the animal. The systems and methods disclosed herein can also enable autonomous monitoring of the structures in the proximity of the cochlea, including, for example, the vestibular system, facial nerves, the carotid artery and the brain.

In one aspect, the new systems for extracting energy from an endocochlear potential of an animal include a circuit coupled to a pair of electrodes connected to endolymph and perilymph, respectively, within a cochlea of the animal. The circuit includes a boost converter that transforms the endocochlear potential across the pair of electrodes to a higher potential, and an energy buffer component connected to the boost converter, the energy buffer component configured to store electrical energy based on the higher potential. The circuit also includes a start-up rectifier configured to provide voltage to the energy buffer component, and a control component configured to provide control signals to the boost converter. The power extracted from the endocochlear potential is equal or larger than the quiescent power of the circuit.

In another aspect, methods for extracting energy from an endocochlear potential of an animal include coupling an electrode to endolymph of the animal and another electrode to perilymph of the animal, in the cochlea, and coupling the two electrodes to a circuit. The coupling applies an input voltage to the circuit by the endocochlear potential. The method also includes initiating operation of the circuit using a power source, converting the input voltage to a higher voltage within the circuit, and storing electrical energy based on the higher voltage.

Implementations of the new methods and systems can include one or more of the following.

The boost converter can include a capacitor, an inductor, and two switches. The boost converter can be configured to convert the endocochlear potential to a higher voltage potential onto the energy buffer component using a trickle charging mechanism. The control component can include a timer and a charge pump circuit, and the charge pump circuit can control the two switches. A radio-frequency transmitter can be coupled to the energy buffer component. The radio-frequency transmitter can be configured to operate with a standby power of 46 pW or less, or with an active cycle of equal or less than 0.0001% of the total duty cycle. The radio-frequency transmitter can be configured to transmit radio data which includes information of the endocochlear potential. The size of the circuit can be 2.4×2.4 mm$^2$ or less, or the quiescent power of the circuit can be less than 660 pW.

The stored electrical energy can be used to operate at least one component of the circuit. The stored electrical energy can be used to operate a device coupled to the circuit. The stored electrical energy can be used to transmit radio data including information of the endocochlear potential. The input voltage can be converted to the higher voltage by a trickle-charging mechanism. The circuit can extract energy from the endocochlear potential at a power of 1.1 nW or larger. Current can be extracted from the animal with a threshold below 100 µA and the current can be used to operate the circuit. The electrical energy can be stored in a capacitor.

The techniques and systems disclosed in this specification provide numerous benefits and advantages (some of which can be achieved only in some of the various aspect and implementations) including the following. Given the new systems, the EP now can be used as power source for operating energy extracting circuits (also referred as "circuits" or "endocochlear chips"). While the EP may be too small to directly power CMOS electronics, the new circuits described herein can convert the EP to a suitable potential for operating electronics. The circuits can also extract small power (avoiding substantial interference with the natural physiology (e.g., hearing) of the animal) from the EP and yet use the energy to operate the circuits or external devices. In addition, the new circuits can be anatomically sized and be implantable in the animals without discomfort.

In general, the disclosed techniques can be used to monitor the EP, which, in turn, can be used to monitor and/or diagnose health conditions of the subject. Circuits may need to be implanted only once without re-implantation for long periods of operation, and thereby reduce surgical risks. Because the new circuits rely on the EP, there may be no need to rely on artificial energy sources (e.g., man-made batteries), which can bring hazards of disconnection or running out of energy unexpectedly. Further, the circuits can be operated without accurate positioning and without maintenance of external devices or batteries, which reduce the risk of radio-frequency (RF) interference, heating of the tissue by transmitted RF power, low cosmesis, and infection.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present technology, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DETAILED DISCLOSURE

The methods and systems described herein can be implemented in many ways. Some useful implementations are described below. The scope of the present disclosure is not limited to the detailed implementations described in this section, but is described in broader terms in the claims.

Endocochlear Potential (EP)

Hearing begins when sound-induced vibrations of the eardrum and middle-ear bones are transmitted to the inner ear fluids, leading to stimulation of sensory hair cells in cochlea of animals. Following the stimulation, neurotransmitter is released, the auditory nerve is excited, and neural impulses are transmitted to the brain.

Figure 1:
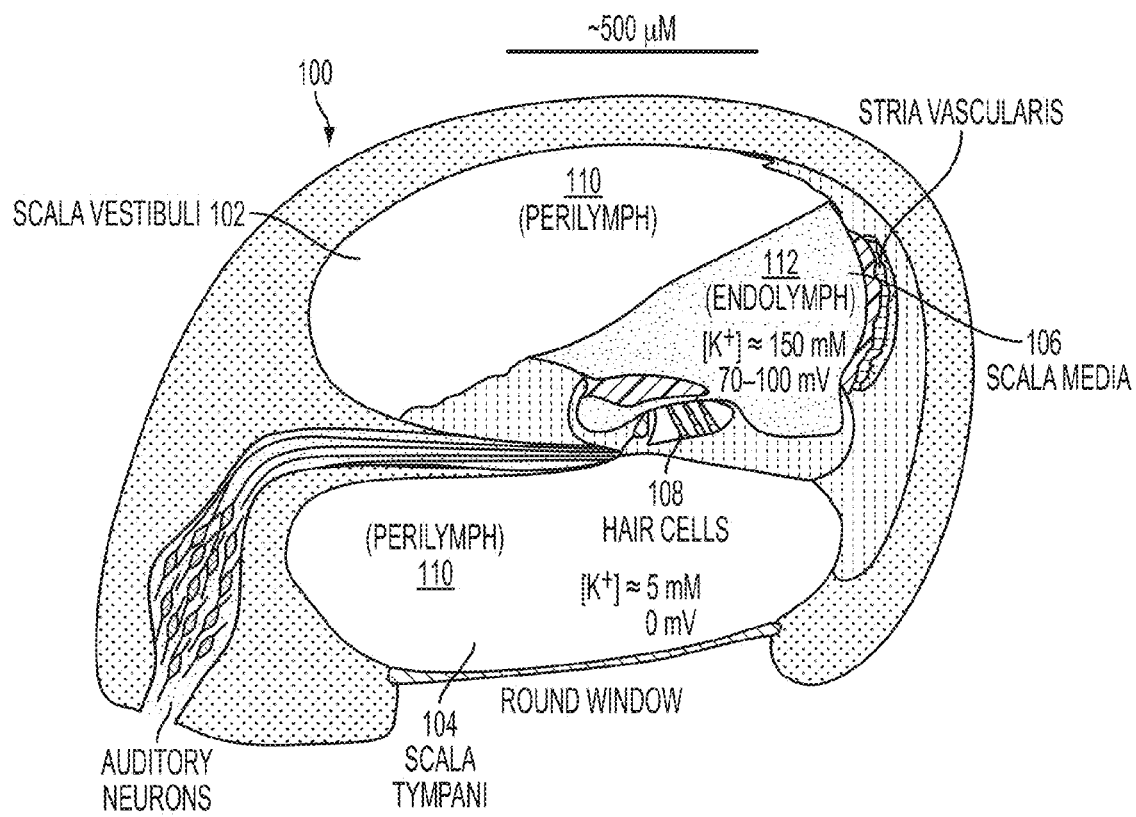
FIG. 1 is a schematic of a cochlea.

FIG. 1 shows a schematic of a cross section of a single turn of a cochlea 100 including a spiral-shaped cavity enclosed by bone and three separate chambers of fluid: scala vestibule 102, scala tympani 104, and scala media 106. The scala vestibuli 102 and scala tympani 104 both contain a fluid called perilymph 110, which is similar in composition to cerebrospinal fluid. The third chamber, the scala media 106, contains a fluid called endolymph 112. The scala vestibuli 102 and scala media 106 fluidic chambers are separated by a thin membrane called Reissner's membrane. The scala tympani 104 is separated from the other chambers by the much thicker basilar membrane. These chambers form an endolymphatic space of the cochlea 100, and surround hair cells 108.

Figure 2:
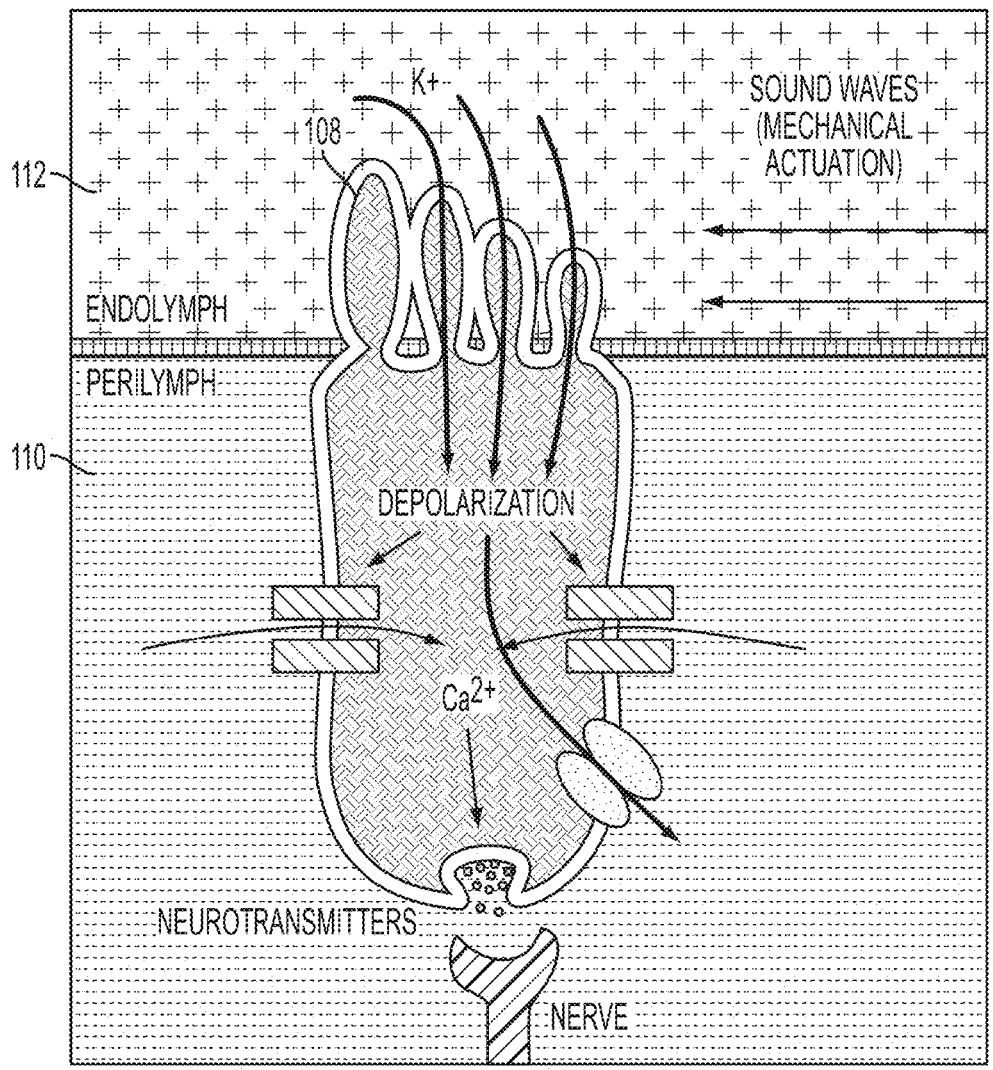
FIG. 2 is a schematic of a hair cell.

The EP is formed in the endolymphatic space of the cochlea 100 (and thus can be referred to as the "EP space"). In particular, the EP is formed between the endolymph 112 (specialized inner ear fluid with a uniquely higher concentration of potassium) and the perilymph 110. As illustrated in FIG. 2, which shows a schematic of an ionic hair cell 108, the endolymph 112 is separated from the surrounding extracellular spaces bathed in the perilymph 110, which is similar in ionic composition to the cerebrospinal fluid, by a complex network of tight junctions. The EP effectively acts as a biologic battery with a potential that is actively stabilized by a specialized arrangement of potassium channels, pumps, and co-transporters in cells of the stria vascularis, which is a specialized structure that borders the endolymphatic space.

The EP is one of the largest positive direct current (DC) electrochemical potential in animals (e.g., mammals including humans) and is the main driving force for cochlear mechano-transduction of sound pressure vibrations to neurotransmitter release and excitation of the auditory nerve. Typically, the EP ranges between 70-100 mV in mammals. This specification relates to extracting energy from electric potential (such as the EP) in animals.

Figure 3:
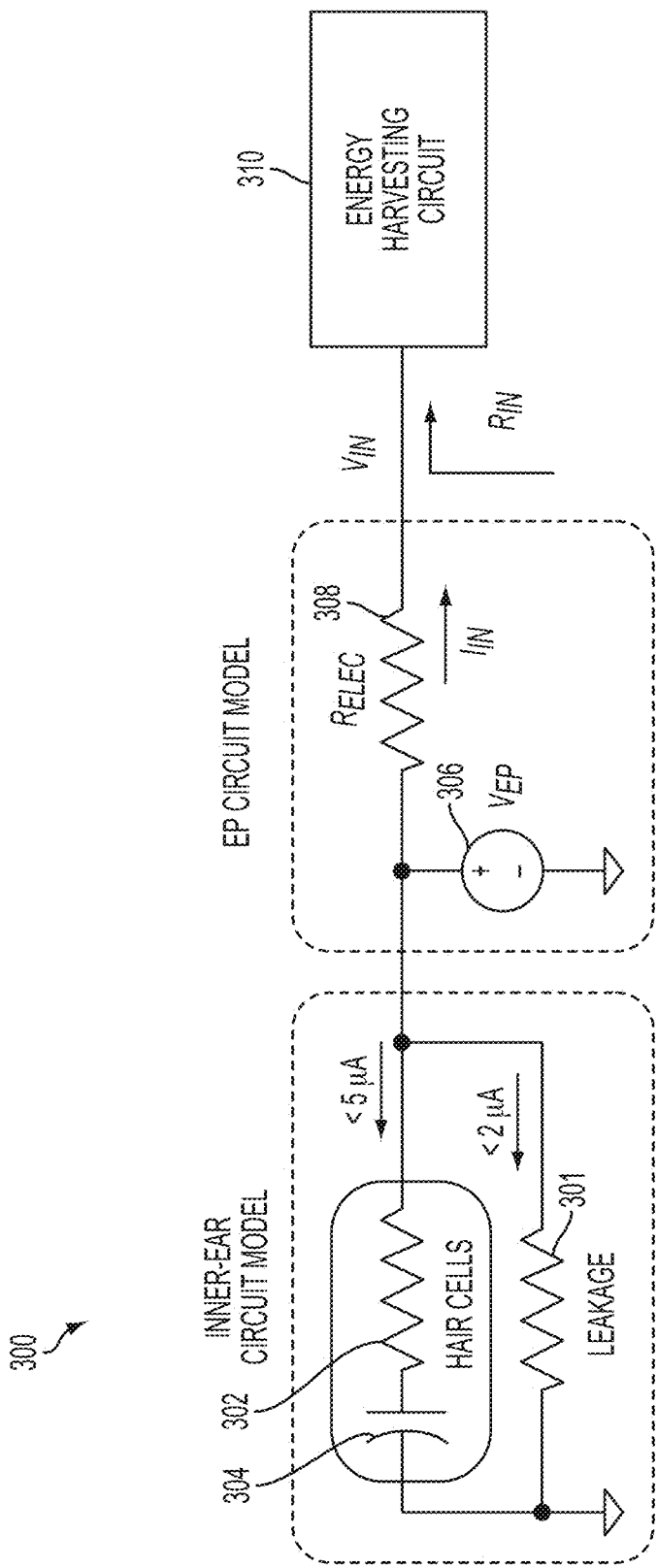
FIG. 3 is a schematic circuit model of the current flow in a cochlea.

FIG. 3 shows a schematic model 300 of the current flow in a cochlea 100, where an energy extracting circuit 310 is coupled to the cochlea 100 by electrodes. The model includes a resistor 301 (representing the tight junction networks) and a resistor 302 in series with a capacitor 304 (representing leakage current through mechanically actuated hair cells). Impedance of an electrode is modeled as resistor $R_{elec}$ 308. Current flow through hair cells 108 ranges between 1-4 µA at quiet to maximal sound intensities (e.g., 0-100 dB). Leakage current through non-sensory cells and the tight junction networks can be about 1 µA. Currents up to about 14-28 µA can flow (generated by natural physiology) in the cochlea 100. The circuit 310 can draw currents from EP 306 that are substantially less than (e.g., 0.1% to 0.01% of) the currents in the range of 14-28 µA. Such low draw current does not affect the hearing performance of the cochlea 100.

Devices

Figure 4:
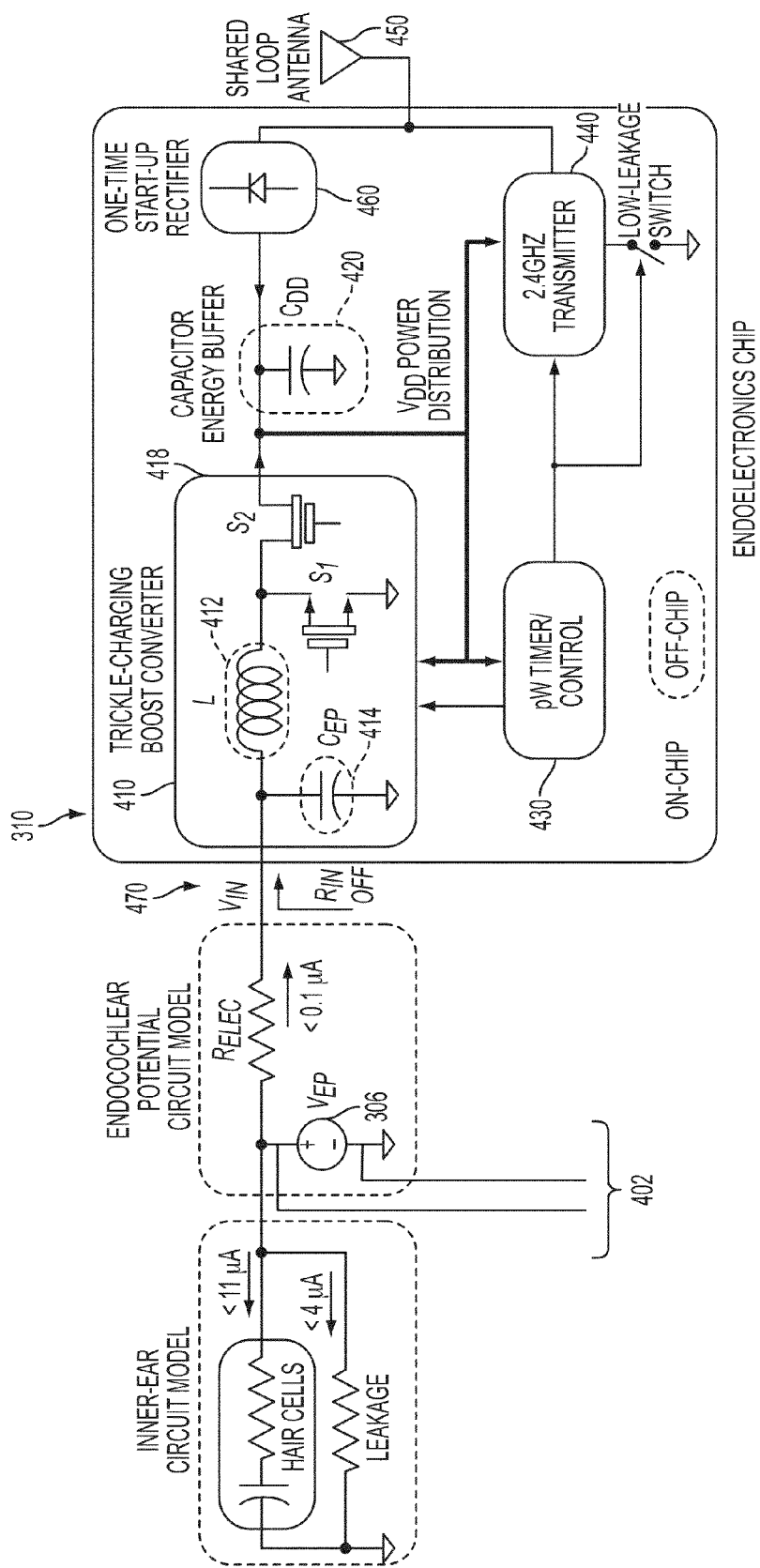
FIG. 4 is the schematic circuit model of FIG. 3 with a detailed view of an energy extracting circuit.

FIG. 4 shows an example of an energy harvesting circuit 310 for extracting energy from EP 306. The circuit 310 includes a boost converter 410 coupled (e.g., electrically connected) to an energy buffer component 420. The boost converter 410 can transform an input voltage 470 received from the EP 306 to a higher voltage within the circuit 310. The energy buffer component 420 can include a capacitor. The circuit 310 can include a control component 430 which provides control signals to the boost converter 410 and/or a radiofrequency (RF) transmitter 440. Further, the energy buffer component 420 can be coupled to a startup-rectifier 460. In some implementations, the RF transmitter 440 and the startup rectifier 460 can be coupled to a loop antenna 450.

In some implementations, the boost converter 410 can include an inductor L 412, a capacitor $C_{EP}$ 414, a switch $S_1$ 416 and a switch $S_2$ 418. The switches $S_1$ 416 and $S_2$ 418 can include transistors. The boost converter 410 can charge the energy buffer component 420 using a trickle-charging mechanism which is described later. For example, in one configuration, the switch $S_1$ 416 is closed (active) and the switch $S_2$ 418 is opened (inactive). The inductor L 412 can be energized due to current flowing into the boost converter 410 from the EP 306. In another configuration, the switch $S_1$ 416 is opened and the switch $S_2$ 418 is closed, and the energy in the inductor L 412 is transferred to induce a voltage (e.g., higher than the EP 306) on the energy buffer component 420. The activation of switches $S_1$ 416 and $S_2$ 418 in relation to the voltage conversion is described later.

A pair of electrodes 402 (also represented by $R_{elec}$) can be used to connect the circuit 310 and the EP space. For example, one electrode can connect the endolymph 112 and the inductor L 412 of the boost converter 410. The other electrode can connect the perilymph 110 as the ground reference. Alternatively, the perilymph 110 can be connected to the inductor L 412 and the endolymph 112 can be connected as the ground reference. In some implementations, the pair of electrodes can have an impedance that is less than 2 MΩ, e.g., less than 1.1 MΩ, less than 0.4 MΩ, or less than 0.2 MΩ. The pair of electrodes can have impedance in the range of 0.6-0.8 MΩ (e.g., 0.4-1.1 MΩ, or 0.2-2 MΩ). The diameter of at least one of the electrodes can be 3 μm or less (e.g., 2 μm or less, 1 μm or less, or 0.5 μm or less). It is understood that at least one of the electrodes can simultaneously satisfy at least some of the disclosed ranges of both the impedance and diameter. The diameter can be chosen to minimize collateral cell damages when inserting the electrodes in the EP space.

The pair of electrodes can be glass electrodes (e.g., glass micropipettes). For example, the glass electrodes can be filled with electrolyte solution (e.g., KCL) being in contact with an Ag/AgCl electrode to allow conversion of ionic into electronic current. These types of electrodes can provide liquid-liquid interface at the electrode tip, which minimizes junction potentials, and provides reliable measurements of DC potentials. Alternatively, the electrodes can be made from plastic or carbon nanotubes (e.g., multiwalled nanotubes and/or nanotubes coated with conducting polymers) which can penetrate cells in a nondestructive manner. In some implementations, the electrodes can be low impedance electrodes with small junction potentials, which are flexible enough to tolerate head movements and rigid enough at the tip to allow stable tissue penetration with minimal damage.

The start-up rectifier 460 (e.g., silicon diode) should be configured to provide voltage to the energy buffer component 420. For example, an external RF source can provide a startup charge packet (e.g., RF electromagnetic fields) to the startup-rectifier 460, which may be referred as a "kick-start" process. The startup charge packet can be converted from RF power to DC power by the startup-rectifier 460, which further energizes the energy buffer component 420 by applying a startup voltage. In some implementations, the startup charge packet can be applied as a one-time process to initially activate the circuit 310. After activating the circuit 310, the boost converter 410 can operate in a self-sustainable manner using energy extracted from the EP 306, without further receiving energy from the external RF source.

During operation, the buffer component 420 can provide the stored energy (e.g., extracted energy from the EP 306), in the form of current, to the RF transmitter 440, which can communicate information (e.g., data bits) to an external monitoring device. The RF transmitter 440 can include a ring oscillator. The RF transmitter 440 can send out information using the loop antenna 450 (e.g., which can have a size of 3 mm×4 mm or less). The loop antenna 450 can also be used to receive the startup charge packet from the external RF source. Such a configuration reduces the circuit 310's physical volume, which is advantageous for an implant circuit 310.

In some implementations, the RF transmitter 440 is operated with an active duty cycle (duration of active transmission mode) to be 0.1% or less (0.01% or less, 0.001% or less, 0.0001% or less) of the total duty cycle (total duration of an active transmission mode and a power standby mode). In some implementations, the standby (inactive) power of the RF transmitter 440 can be less than 50 pW. For example, the standby power can be about 46 pW at 0.9 V. The output data rate of the RF transmitter 440 can be determined by the included ring oscillator. For example, the RF transmitter 440 can operate at instantaneous data rates programmable from 100 kbps to 10 Mbps up to a 1 m distance.

The system also includes a control component 430, which can include a timer (e.g., relaxation oscillator), a control circuitry, and a charge-pump circuit. The charge-pump circuit can be used to drive the switches $S_1$ 416 and $S_2$ 418 roughly double of $V_{DD}$ (i.e., voltage of the energy buffer component 420). This limits the amount of reverse leakage (and reduces power consumption) through the switches $S_1$ 416 and $S_2$ 418 during long periods of time when either of the switches are turned off.

In some implementations, the RF transmitter 440 can include a ring oscillator, cross-coupled pair of transistors, and a capacitive tuning digital-to-analog converter (DAC). The ring oscillator can operate from 100 kHz to 10 MHz. The loop antenna 450 can be sized to fit with the anatomical constraints of the subject. In some implementations, the loop antenna 450 can operate as a resonant (for receiving the startup charge packet) and a radiative (for transmitting data) element. The loop antenna 450 can be optimized to have maximum transmitter radiation efficiency.

Figure 6:
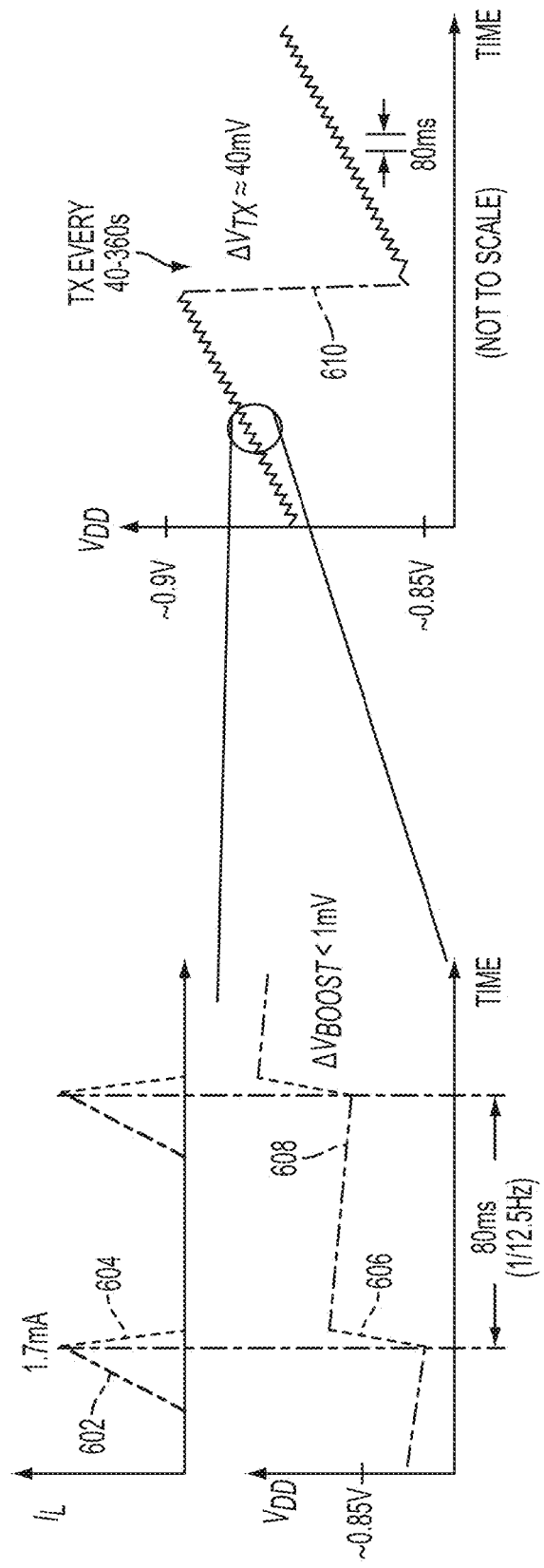
FIG. 6 is an exemplary time diagram of voltage conversion.

FIG. 6 illustrates an exemplary time diagram of the voltage conversion by the boost converter 410. The timer (in control component 130) generates a clock signal (e.g., 12.5 Hz) used to generate signals to control switches $S_1$ 416 and $S_2$ 418. For example, the clock can be passed through a pulse generator included in control circuitry of the control component 430 to create a first signal that directly controls switch $S_1$ 416. When signal $S_1$ 416 is high, current through inductor L 412 is being ramped up, as indicated as 602 in FIG. 6. At this stage, energy is being stored in the magnetic field of the inductor L 412. When switch $S_1$ 416 is turned off, switch $S_2$ 418 is turned on by a second signal provided by the control component 430. At this stage, energy stored on inductor L 412 is transferred to the energy buffer component 420 with increasing voltage VDD (indicated by 606 in FIG. 6). Simultaneously, current in the inductor L 412 will ramp down (e.g., to zero current), which is indicated as 604, and switch $S_2$ 418 will be closed. The duration of this process can depend on the clock signal of the timer. For example, the periodic duration can be about 80 ms. During the time when switch $S_2$ is closed, some energy stored on the energy buffer component 420 can leak (indicated by 608 in FIG. 6), which can be modeled as a load resistor. The overall process can be referred as a "trickle-charge mechanism."

As long as the energy coming from the input voltage induces a larger voltage on the energy buffer component 420 than the leak voltage, energy can be built up over time. Energy stored in the energy buffer component 420 can be used to drive the RF transmitter 440, which leads to a drop in the voltage of the energy buffer component 420 as indicated as 610 in FIG. 6. As long as the RF transmitter's 440 power consumption is less than or equal to the energy stored in energy buffer component 420 since the last radio data transmission, the circuit 310 can sustain itself.

In some implementations, the circuit 310 can be operated in a self-sustainable manner using energy extracted from EP 306. For example, switches $S_1$ 416 and $S_2$ 418 can have quiescent (e.g., when inactive) power consumption less than 50% (e.g., less than 20%, less than 10%, less than 1%) of the output power of the boost converter 410. Generally, one or more components (e.g., transistors, switches, timers) of the circuit 310 can be fabricated using leakage reduction techniques. For example, the oxide thickness, transistor width, and length can be selected for low-leakage of currents during standby mode.

Fabrication

One or more of the components (e.g., transistors, switches, logic gates, capacitors, inductors) of circuit 310 can be fabricated using standard or otherwise known semiconductor fabrication techniques with an appropriate minimum feature size, e.g., metal-oxide-semiconductor (CMOS) processes with a minimum feature size of 0.18 µm. This can allow fabrication of components with low-leakage characteristics. The 0.18 µm an technology can be used to realize a fully functional circuit with low standby power consumption with high frequency performance (about 2.4 GHz), as well as providing thick-oxide high threshold voltage devices with low-leakage currents.

General Methodology

Figure 5:
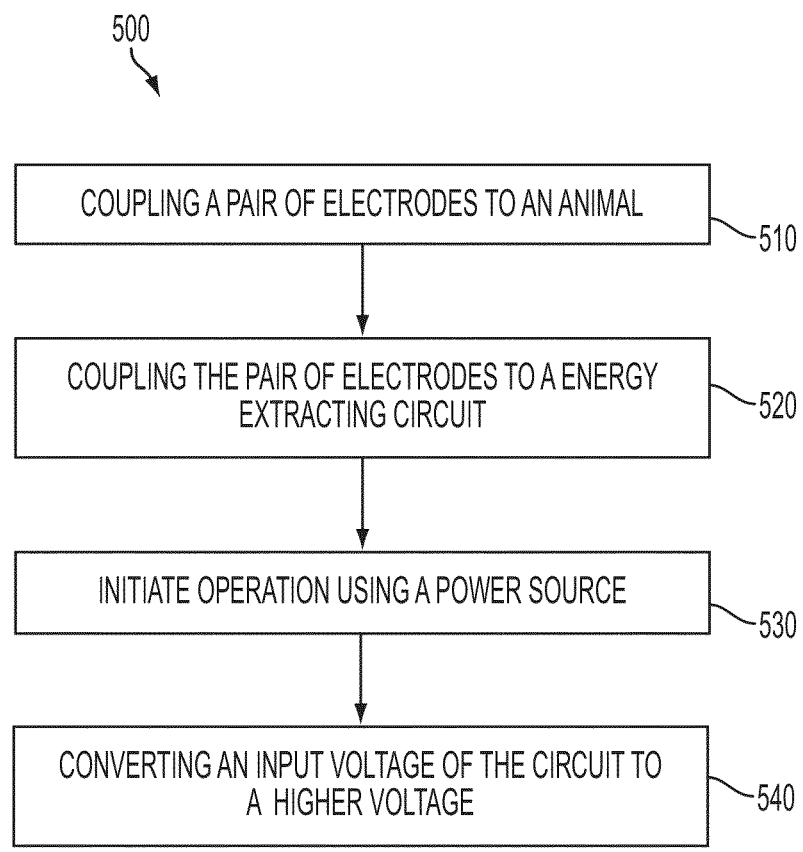
FIG. 5 is a flow chart depicting exemplary sequence of operations for extracting energy.

Referring to FIG. 5, a flow chart 500 depicts exemplary operations for extracting energy from EP 306. Operations include coupling (e.g., connecting) a pair of electrodes to an animal (510). In some implementations, a positive electrode is connected to an endolymph 112 of a subject and a negative electrode is connected to a perilymph 110 of the subject. Alternatively, the negative and positive electrodes may be reversed.

Operations also include coupling the two electrodes to a circuit 310, where the coupling applies an input voltage to the circuit 310 by the endocochlear potential (520). In some implementations, the positive electrode is connected to an input of a boost converter 410 in the circuit 310 and the negative electrode is grounded with reference to the perilymph 110. Alternatively, the negative and positive electrodes are reversed. In some implementations, the endolymph 112 can be the ground reference instead of the perilymph 110.

In some implementations, impedance ($R_{elec}$) of the two electrodes are configured to be as close to the impedance ($R_{in,eff}$) of the circuit 310 as feasible to maximize the extractable power from the EP 306 to the circuit 310, which can be presented as:

$$P = V_{IN}^2/R_{in,eff} = [V_{EP}/(R_{in,eff}+R_{elec})]^2 \times R_{IN,eff} \quad (1)$$

where $V_{EP}$ is the endocochlear potential, and $V_{IN}(=V_{EP} R_{in,eff}/(R_{in,eff}+R_{elec}))$ is the input voltage to the circuit 310. To maximize the extractable power given electrode impedance constraints, $R_{in,eff}$ needs to be configured close to $R_{elec}$. In some implementations using glass microelectrodes, the tradeoff between electrode impedance and bluntness (determined for avoiding cell damages) reaches a point of diminishing returns around $R_{elec}$=0.4-1.5 MΩ. For this range, the extractable power can range from 0.6-6.3 nW with $V_{IN}$ in the range of 30-55 mV, and extractable current in the range of 20-125 nA. The maximum extractable power from the EP 306 to the circuit 310 can be well below this range when using high impedance electrodes. Such electrodes can be designed to have sharp tips and can minimize collateral cell damage when inserted into the EP space.

The maximum extractable power can be presented as:

$$P_{max} = V_{EP}^2/(4R_{elec}), \quad (2)$$

Operations also include initiating operation of the circuit 310 using a power source (530). In some implementations, the power source can be an external RF source which can provide a startup charge packet for initiating the operation of the circuit 310. For example, the initiating can include a kick-start process as described herein.

Operations also include converting the input voltage to a higher voltage within the circuit 310 (540). In some implementations, the input voltage is received by a boost converter 410 in the circuit 310, and the input voltage is converted to the higher voltage larger than the input voltage. A control component 430 sends control signals to the boost converter 410 to open-close switches $S_1$ 418 and $S_2$ 418 included in the boost converter 410. When $S_1$ 416 is closed and $S_2$ 418 is opened, the higher voltage can be form on an inductor included in the boost converter 410. When $S_1$ 416 is opened and $S_2$ 418 is closed, the higher voltage can be passed over to an energy buffer component 420 in the circuit 310.

In some implementations, operations can include using the higher voltage to operate at least one component of the circuit 310. For example, the switches $S_1$ 416, $S_2$ 418, RF transmitter 440, and/or the control component 430 can be operated using the higher voltage formed on the energy buffer component 420. Alternatively, the higher voltage can be used to operate a device external to the circuit 310. For example, the device can be a separate sensor or transmitter. In some implementations, the higher voltage can be used to transmit radio data which includes information of the endocochlear potential. The radio data can be monitored to determine relative changes in the EP 306.

In some implementations, operations can include measuring compound action potential thresholds using tone-pip audiograms to determine the performance of hearing of the animal.

General Applications

Energy harvested from the EP can be used to measure relative changes in the EP by monitoring the voltage drop on the electrode resistor 308 (e.g., input voltage $V_{IN}$). The wirelessly transmitted data bits from the RF transmitter 440 can inherently encode EP information. This is because the instantaneous radio data rate can be generated internally by a ring oscillator whose frequency varies with $V_{DD}$ (which in turn varies with the EP and input voltage $V_{IN}$). Accordingly, the circuit can be a self-powered system that is capable of continuously monitoring relative changes in the EP.

The disclosed techniques can be applied in animal studies for biotechnology and medicine. For example, the energy extracting circuits can be utilized as miniaturized and fully implantable sensing systems with minimal risk of malfunction from external infections or trauma for small rodents commonly used in hearing research.

The circuits can be utilized as chemical or electronic sensors and actuators implanted, e.g., in nearby vestibular organs of the inner ear. The implanted location need not be limited to the cochlea, but also in the adjacent structures such as the temporal lobe of the brain, facial nerve, and carotid artery, all of which are within millimeters of the cochlea.

The disclosed techniques can be used with human cochleas. The surgical insertion of devices, such as cochlear implants and stapes prostheses, into the human inner ear is already possible with minimal risks of damaging normal or residual hearing. Thus, implantation of the presently described devices should also be possible.

On the other hand, loss of sensory cells, cochlear neurons, or supporting cells can lead to various forms of deafness where the EP is normal. In such cases, a battery-less system such as the energy extracting circuit for sensing various parameters, e.g., of key molecules in the inner ear, can be beneficial with no additional risk given the pre-existing loss of hearing. In some applications, energy extracted from the EP can function as a "biologic battery" that powers chemical sensors or drug-delivery actuators to enable diagnostics and therapies. For example, the energy extracted from the EP can be used for dual sensing and actuation of pumps for intracochlear delivery of growth factors, small molecules and other therapies to induce regeneration in ears that are already deaf. Close sensing of the cochlea during intracochlear delivery of regenerative therapies can provide critical information to prevent transformation to cancer.

EXAMPLES

The methods and systems described herein are further illustrated using the following examples, which do not limit the scope of the claims.

Example 1

An Energy Extracting Circuit

Figure 7:
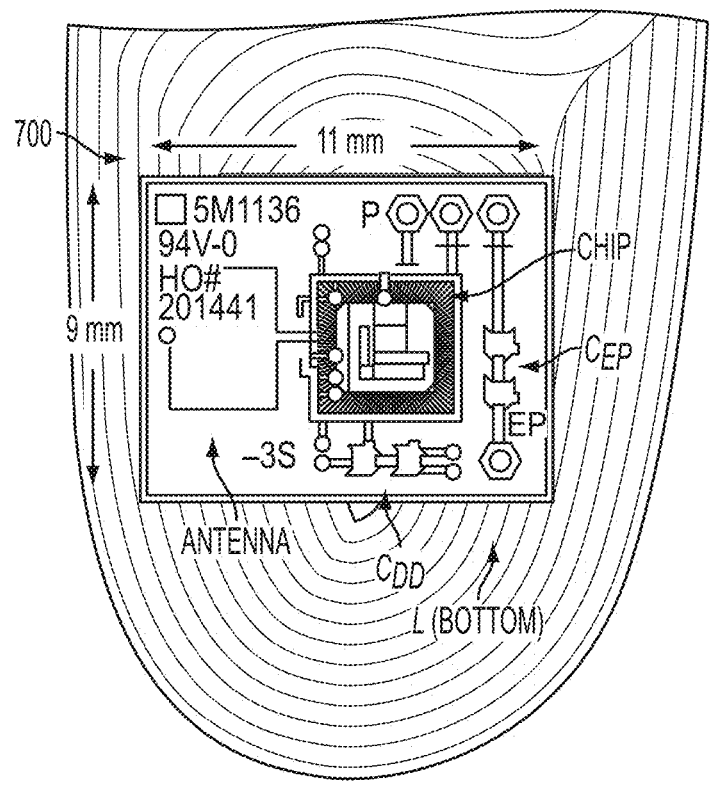
FIG. 7 is an exemplary energy extracting device.

FIG. 7 shows an exemplary energy extracting device 700 including an energy extracting circuit 310, which occupied a volume of less than 2.4×2.4×0.2 mm³ (excluding components such as the antenna or bulk capacitors). The circuit 310 was wire-bonded on a printed circuit board manufactured with an FR-4 substrate, which is sufficiently small to be implantable in the human mastoid cavity or in the bulla cavity of cats, gerbils, or chinchillas. Parts of the components were fabricated using CMOS technology. Two capacitors and an inductor 412 were mounted on the printed circuit board. A loop antenna 450 was printed on the printed circuit board. The circuit 310 was encapsulated by a non-conductive epoxy (not shown) for mechanical stability. The system supply voltage was measured during in vivo experiments using a Keithley 2602 sourcemeter, while $V_{IN}$ was measured using an Agilent U1253A multimeter set to 1 GΩ input impedance. A wireless receiver, which was built using discrete components, was used to down-convert and record the instantaneous transmitter data rate on a Tektronix TDS3064B oscilloscope. The chip power consumption was measured during characterization experiments using a Keithley 6430 sourcemeter and high-isolation triaxial cables for accurate low-current measurements.

Example 2

In vivo Testing of an Energy Extracting Circuit

Surgical procedures were carried out to connect energy extracting circuits 310 to the cochlea of Hartley Albino *Cavia porcellus* (guinea pigs). The animals were anesthetized and experiments were conducted in a heated, acoustically insulated chamber. Most animals had spontaneous, natural breathing. Mechanical ventilation was only used if respiration faltered due to anesthesia. The auricle and neighboring musculature were reflected ventrally to expose the external auditory meatus and bulla. The lateral wall of the bulla, up to the caudal edge of the tympanic ring, was removed to allow visualization of and access to the round window. Pulled glass microelectrodes, mounted on micromanipulators, were advanced through the round window to access the fluid spaces of the inner ear. One (negative) electrode was inserted into the perilymph-filled scala tympani, and the other (positive) electrode was inserted through the basilar membrane and sensory epithelium into the endolymph-filled scala media.

The electrodes were pulled from Borosil capillary tubing (FHC, Bowdoin, Me.). The tips of electrodes were beveled at a 25° angle using a BV-10 Microelectrode Beveler (Sutter Instruments, Novato, Calif.) to achieve tip diameters of about 2 μm with electrode impedance of 400-800 kΩ for both electrodes. Electrodes were mounted in half-cell holders containing Ag/AgCl exchange pellets (World Precision Instruments, Sarasota, Fla.). Electrolyte composition was 2 M KCl. All circuit grounds were with reference to perilymph 110.

The energy extracting circuit 310 was operated up to five hours in the guinea pig model. Initially, an external RF source operating at 2.4 GHz and placed several millimeters away was used to wirelessly start (a kick-start process for two second or less) the operation of the circuit 310, addressing the low-voltage turn-on issue. Due to on-chip voltage clamps, an energy buffer component 420 ($C_{DD}$), which had a capacitance of 200 nF, charged to at most 1.4 V during initialization. At 1.4 V, energy buffer component 420 was storing $E=0.5C_{DD}V_{DD}^2=200$ nJ of energy.

During operation, a boost converter 410, a RF transmitter 440, and peripheral components consumed about 573 pW at 0.9 V. At this power consumption, the circuit 310 would theoretically operate for at most 6 minutes before completely exhausting the energy stored on energy buffer component 420 ($C_{DD}$). The control component 430 utilized a 300 pW continuously running timer and control circuitry that consumed 527 pW at 0.9V, and the control component 430 generated pulses every 45-360 seconds to the RF transmitter 440. The RF transmitter 440 communicated at 1.67 Mbps over a 1l distance while consuming 75 pJ per transmitted bit. In this measurement, the RF transmitter 440 spends less than 0.00001% of the total duty cycle in active mode, with packets of 64 to 128 bits, transmitted once every 45-360 seconds. The boost converter 410 extracted 60-2840 pW of net positive power from the EP, taking account of the power consumption from the control.

Figure 8:
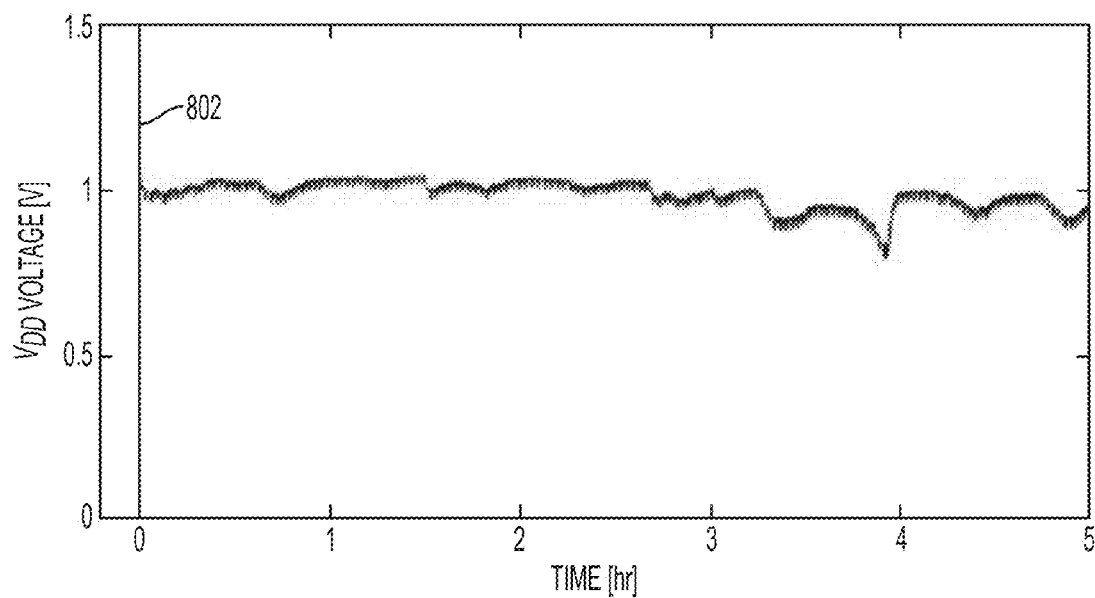
FIG. 8 is a plot showing measured results of voltage of an energy buffer component.

For feasibility studies, the circuit 310 was operated externally, with electrode tips inserted into the cochlea 100 and the electrode shafts connected to the circuit 310. FIG. 8 shows the buffer component 420 supply voltage ($V_{DD}$), which replenished and persisted throughout a five hour measurement. Because the circuit 310 operated longer than the energy contained in the initial kick-start process otherwise permitted (which is at most 6 min), these results demonstrate that the circuit 310 is powered from the EP 306. The sharp peak 802 indicated the voltage increase by the kick-start process. As the boost converter 410's average input impedance was configured to approximately equal the electrode impedance, the boost converter 410 extracted close to the maximal possible power from the EP given physical constraints of electrodes. As a result, the $V_{DD}$ slowly fluctuated as the animal's EP and the available energy varied.

Figure 9:
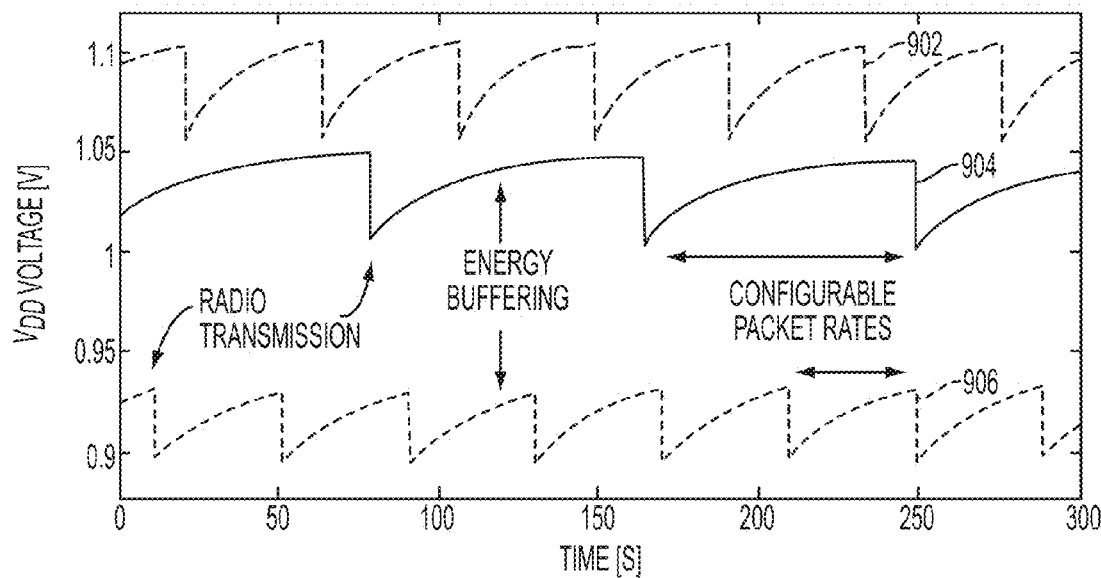
FIG. 9 is a plot showing measured results of voltages of energy buffer components for three different animals.

FIG. 9 shows measurement results from three different animals 902, 904 and 906—the $V_{DD}$ periodically dropped by 36-48 mV during active-mode wireless transmissions. Following the drop, the boost converter 410 continued to harvest energy from the EP by trickle-charging capacitor CDD, thereby recovering energy (which ramped up $V_{DD}$) spent during the transmission.

Monitoring the Relative Change of EP

Figure 10:
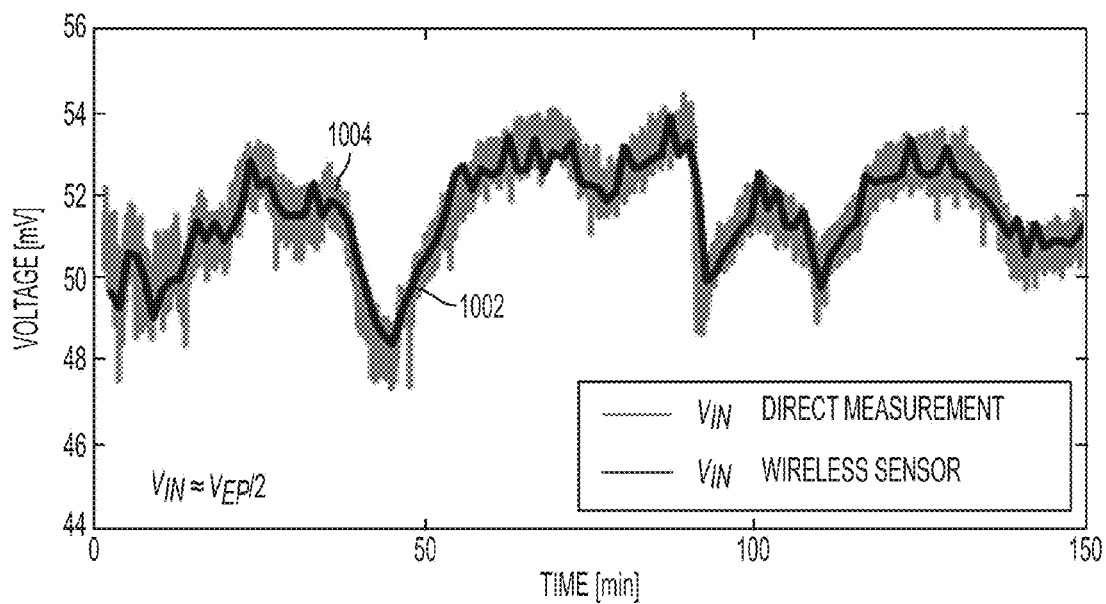
FIG. 10 is a plot showing measurement results of input voltage $V_{IN}$.

Relative change in the EP can be estimated from the instantaneous data rate transmitted by the RF transmitter 440. FIG. 10 compares the estimated results 1002 for input voltage ($V_{IN}$) using the relation:

$$V_{IN}=V_{EP}R_{in,eff}/(R_{in,eff}+R_{elec})), \quad (3)$$

as deduced from the instantaneous data rate and the directly measured results 1004 of the input voltage. The estimated results were within a 0.45 mV RMS error of the direct measurements over a 2.5 hour experiment.

Example 3

Tone Pip Audiograms

To test whether the circuit 310 affected hearing performance of the guinea pig, compound action potential thresholds were measured before and after electrode insertion. The cochlear function was tested along its length by using tone pips of different frequencies because the cochlea is tonotopically organized, with the high frequencies encoded at the cochlear base and low frequencies encoded at the cochlear apex. Tone-pip audiograms were measured by presenting brief tones (3.0 ms duration, 0.5 ms rise/fall times), at half-octave spacing between 2-32 kHz, to the external ear canal of the surgically targeted ear. The resulting compound-action potential was recorded using a metal-wire electrode placed adjacent to the round window. The threshold was defined as the minimum sound intensity required to elicit a response above 10 µV (the noise floor was measured to be approximately 4 µV).

Figure 11A:
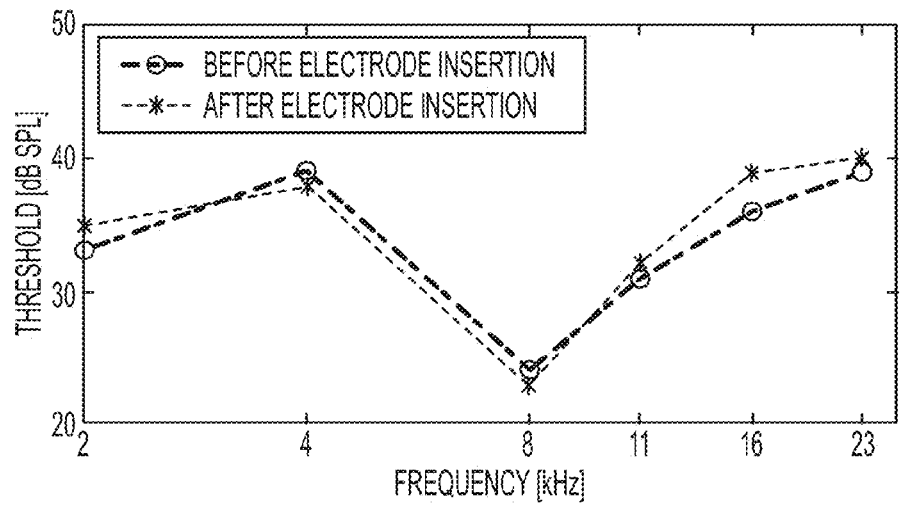
FIGS. 11A and 11B are plots showing measurement results of compound action potential thresholds.
Figure 11B:
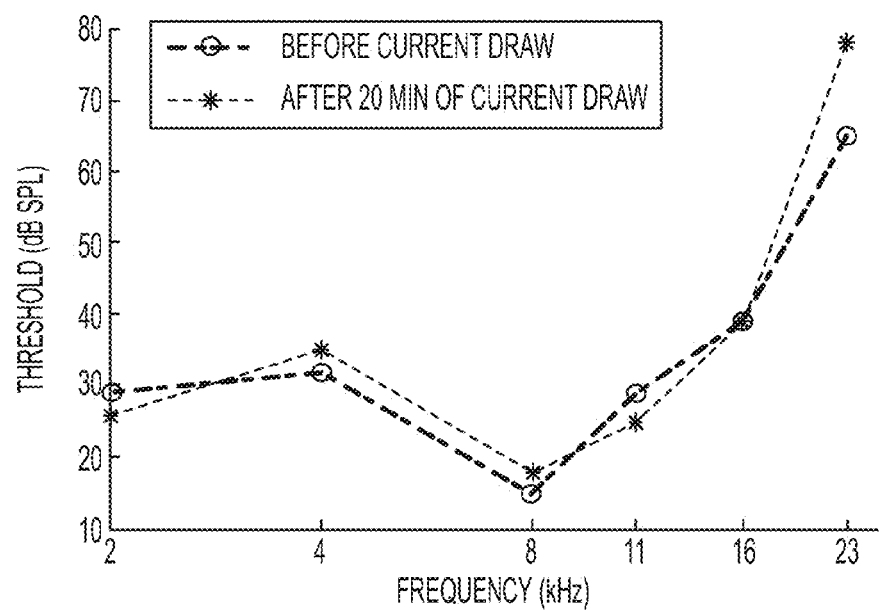

FIG. 11A shows that the insertion of the electrodes did not adversely affect hearing—the audiogram data before and after the insertion is substantially similar. FIG. 11B shows the measured compound action potential thresholds before and after current draw. The current draw results show that the operation of the circuit 310 did not have substantial effect on hearing for frequencies up to 16 kHz. A small degradation in threshold was observed at a frequency of 23 kHz, which is encoded close near the cochlear base. This degradation is likely due to the electrode tip, which was designed to be about 2 µm in diameter after beveling so to allow low electrode impedance of about 800 kΩ. At such sizes, electrodes can cause local physical trauma to the cells lining the basilar membrane and can allow leakage of ions across the endolymph-perilymph barrier, as well as leakage of ions from the fluid-filled electrodes into cochlear fluids.

In other examples, electrodes with tips diameters smaller than 1 µm and impedances larger than 5 MΩ were used to stably record the EP 306 for many hours.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for extracting energy from an endocochlear potential of an animal, the system comprising:
    a first electrode having an end to contact endolymph within a cochlea of an animal;
    a second electrode having an end to contact perilymph within the cochlea of the animal; and
    an energy harvesting circuit comprising:
        a boost converter that transforms an endocochlear potential across the first electrode and the second electrode to a higher potential;
        an energy buffer component connected to the boost converter to store electrical energy transformed by the boost converter;
        a control component providing control signals to the boost converter and powered by the energy buffer;
        an antenna; and
        a start-up rectifier that receives an external signal via the antenna to provide an initial voltage to the energy buffer component.

2. The system of claim 1, wherein the boost converter comprises:
    an inductor having a first end coupled to one of the first electrode and the second electrode;
    a first switch coupled to a second end of the inductor; and
    a second switch coupled between the second end of the inductor and the energy buffer component, wherein the first switch and the second switch receive the control signals from the control component.

3. The system of claim 2, wherein the control component comprises:
    a timer generating clock signals; and
    a charge pump circuit driving the first switch and the second switch according to the clock signals.

4. The system of claim 1, wherein the boost converter converts the endocochlear potential to a higher potential using a trickle charging mechanism comprising a periodic cycle of storing energy from the endocochlear potential in the boost converter followed by transferring the energy to the energy buffer component.

5. The system of claim 1, further comprising a radio-frequency transmitter coupled to the control component and the antenna, wherein the radio-frequency transmitter operates with a standby power of 46 pW or less, or with an active cycle of equal or less than 0.0001% of a total duty cycle.

6. The system of claim 5, wherein the radio-frequency transmitter is further coupled to the energy buffer component to receive power to operate, the radio-frequency transmitter transmitting radio data that includes information of the endocochlear potential.

7. The system of claim 1, wherein a size of the circuit is 2.4×2.4 mm² or less, or the quiescent power of the circuit is less than 660 pW.

8. The system of claim 1, wherein the energy harvesting circuit is fully implantable in the animal.

9. The system of claim 1, wherein the first electrode and the second electrode each comprises a glass electrode filled with electrolyte solution contacted with an Ag/AgCl electrode.

10. The system of claim 1, wherein the first electrode and the second electrode each comprises plastic or carbon nanotubes shaped to penetrate cells in a nondestructive manner.

11. A method of using an endocochlear potential of an animal as an energy source, the method comprising:
    contacting a first electrode to endolymph within a cochlea of the animal and a second electrode to perilymph within the cochlea of the animal, wherein the first electrode and the second electrode are coupled to an energy harvesting circuit and an endocochlear potential across the first electrode and the second electrode applies an input voltage to the energy harvesting circuit, wherein the energy harvesting circuit comprises:
        a boost converter that transforms the endocochlear potential across the first electrode and the second electrode to a higher potential;

an energy buffer component connected to the boost converter to store electrical energy transformed by the boost converter;

a control component providing control signals to the boost converter and powered by the energy buffer;

an antenna; and a start-up rectifier that receives an external signal via the antenna to provide an initial voltage to the energy buffer component;

applying the external signal to initiate operation of the energy harvesting circuit;

converting the input voltage to the higher voltage within the energy harvesting circuit; and storing, at the energy buffer component, electrical energy based on the higher voltage.

12. The method of claim 11, further comprising:

using the stored electrical energy to operate at least one component of the energy harvesting circuit.

13. The method of claim 11, further comprising:

using the stored electrical energy to operate a device coupled to the energy harvesting circuit.

14. The method of claim 11, further comprising:

using the stored electrical energy to transmit radio data including information of the endocochlear potential.

15. The method of claim 11, wherein converting the input voltage to the higher voltage within the circuit comprises:

performing a trickle-charging mechanism comprising a periodic cycle of storing energy from the endocochlear potential in the boost converter followed by transferring the energy to the energy buffer component.

16. The method of claim 11, wherein the energy harvesting circuit extracts energy from the endocochlear potential at a power of 1.1 nW or larger.

* * * * *